United States Patent
Li et al.

(10) Patent No.: US 9,122,773 B2
(45) Date of Patent: Sep. 1, 2015

(54) MEDICAL INFORMATION DISPLAY APPARATUS AND OPERATION METHOD AND PROGRAM

(71) Applicant: FUJIFILM Corporation, Tokyo (JP)

(72) Inventors: Yuanzhong Li, Tokyo (JP); Tsuyoshi Hirakawa, Tokyo (JP); Takuya Ebina, Tokyo (JP); Jun Masumoto, Tokyo (JP); Hajime Shirasaka, Tokyo (JP)

(73) Assignee: FUJIFILM CORPORATION, Tokyo (JP)

( * ) Notice: Subject to any disclaimer, the term of this patent is extended or adjusted under 35 U.S.C. 154(b) by 215 days.

(21) Appl. No.: 13/722,945

(22) Filed: Dec. 20, 2012

(65) Prior Publication Data
US 2013/0111387 A1    May 2, 2013

Related U.S. Application Data

(63) Continuation of application No. PCT/JP2012/003283, filed on May 18, 2012.

(30) Foreign Application Priority Data

May 26, 2011 (JP) ................................ 2011-117542

(51) Int. Cl.
*G06F 3/048* (2013.01)
*G06F 19/00* (2011.01)
(Continued)

(52) U.S. Cl.
CPC .............. *G06F 19/32* (2013.01); *G06F 19/321* (2013.01); *G06F 19/322* (2013.01); *G06Q 50/24* (2013.01)

(58) Field of Classification Search
CPC . G06F 19/321; G06F 19/322; G06F 19/3487; G06F 19/3406; G06F 8/34; G06F 3/0481; G06F 3/04847; G06Q 50/22; G05B 19/0426; G05B 2219/23258
USPC ....................................................... 715/771
See application file for complete search history.

(56) References Cited

U.S. PATENT DOCUMENTS 7,978,890 B2    7/2011  Yamagishi et al.
8,392,419 B2 *  3/2013  Heaton et al. ................. 707/737
(Continued)

FOREIGN PATENT DOCUMENTS

CN    101040801 A    9/2007
CN    101320991 A    12/2008
(Continued)

OTHER PUBLICATIONS

Chinese Office Action dated Jan. 16, 2014, with English translation.
(Continued)

*Primary Examiner* — Nicholas Augustine
(74) *Attorney, Agent, or Firm* — McGinn IP Law Group, PLLC (57) ABSTRACT

A predetermined period is selected on timeline, and electronic medical record information about examination and treatment received by a predetermined person to be examined during the selected period is retrieved. All of examined regions recorded in the electronic medical record information are extracted therefrom. Further, external view image representing an external view of the person to be examined is displayed, and marks representing the examined regions are superimposed at the positions of the examined regions in the external view image.

17 Claims, 8 Drawing Sheets

(51) Int. Cl.
*G06Q 50/24* (2012.01)
*G06F 3/00* (2006.01)

(56) References Cited

U.S. PATENT DOCUMENTS

| | | | |
|---|---|---|---|
| 8,762,102 B2* | 6/2014 | Yuen et al. | 702/160 |
| 8,771,206 B2* | 7/2014 | Gettelman et al. | 600/587 |
| 2005/0131737 A1 | 6/2005 | Joseph et al. | |
| 2006/0215897 A1* | 9/2006 | Ando | 382/132 |
| 2008/0208624 A1 | 8/2008 | Morita et al. | |
| 2008/0243548 A1* | 10/2008 | Cafer | 705/3 |
| 2008/0267481 A1 | 10/2008 | Nakamura | |
| 2009/0054755 A1* | 2/2009 | Shiibashi | 600/407 |
| 2011/0002515 A1 | 1/2011 | Futami et al. | |
| 2011/0161854 A1* | 6/2011 | Shukla | 715/771 |
| 2012/0029943 A1* | 2/2012 | Kurahashi | 705/3 |
| 2012/0131507 A1* | 5/2012 | Sparandara et al. | 715/833 |
| 2013/0024208 A1* | 1/2013 | Vining | 705/3 |

FOREIGN PATENT DOCUMENTS

| | | |
|---|---|---|
| JP | 2002-117141 A | 4/2002 |
| JP | 2003-260030 A | 9/2003 |
| JP | 2008-234272 A | 10/2008 |
| JP | 2008-259682 A | 10/2008 |
| JP | 2009-119000 A | 6/2009 |
| JP | 2011-010889 A | 1/2011 |

OTHER PUBLICATIONS

Chinese Office Action dated Apr. 30, 2014, with English translation.
Chinese Office Action dated Jun. 6, 2013, with English translation.
Extended European Search Report dated Sep. 23, 2014.

* cited by examiner

MEDICAL INFORMATION DISPLAY APPARATUS AND OPERATION METHOD AND PROGRAM

TECHNICAL FIELD

The present invention relates to techniques for displaying medical information desired by a user by using a graphical user interface.

BACKGROUND ART

In the field of practice of medicine, various kinds of medical information, such as text information in a chart or the like, are stored and accumulated as electronic data. The various kinds of medical information include images obtained by a modality, such as a CT, MRI, US, and PET, waveform information about an electrocardiogram, brain waves or the like, and various examination reports.

In recent years, some system was provided to make it possible to retrieve medical information stored in an individual server of each medical institution from other medical institutions through a service center. For example, the service center manages the location of medical information, such as a server of a specific medical institution storing information about a specific patient. Further, the service center manages link to patients' numbers (patients' ID's) of each medical institution, a right to access medical information, and the like. Further, a medical institution that provides information, such as a major hospital in an area, and institutions that retrieve information, such as a clinic, are connected to each other through a network, such as VPN and SSL, in which the security of communication is secured.

When each medical institution inputs a patient's ID of a patient about whom information is to be shared, medical information about the patient scattered in different medical institutions in the area is displayed as a list. Each medical institution can retrieve medical images by DICOM Viewer in addition to prescription data and examination data. Further, it is possible to share document files and the like. Information is accessible also from an information retrieval institution, such as a clinic.

As a method for easily selecting and checking a massive amount of medical information, as described above, various user interfaces have been proposed. For example, a region in a human body shape or an image representing a partial human body displayed on a display screen is selected by a pointing device. Then, medical images related to a diseased region in the selected region or in the vicinity of the selected region are extracted from a medical information database, and the extracted medical images are displayed as a list (for example, Japanese Unexamined Patent Publication No. 2003-260030 (Patent Document 1)).

Further, a method using an input device including a touch-panel-type display connected to a workstation for medical image processing is known. In the method, when a base line is generated in an axial slice image by a touch operation at the input device, a coronal image sliced at the generated base line is generated and displayed (for example, Japanese Unexamined Patent Publication No. 2009-119000 (Patent Document 2)).

Meanwhile, when a patient is treated, past diseases of the patient, and treatments performed for the diseases may greatly influence treatment that will be performed on the patient. Therefore, doctors want to refer to patient's medical information in the past in addition to information about a currently treated region.

However, the user interface disclosed in Patent Document 1, which tries to obtain more medical information, aims at obtaining information only about a region. Therefore, it is impossible to obtain information about a disease in a different region. Further, the user interface disclosed in Patent Document 2 is used to switch an image that has been selected to a different image. Therefore, it is impossible to check what kind of image is present besides the selected image.

DISCLOSURE OF INVENTION

In view of the foregoing circumstances, it is an object of the present invention to provide a medical information display apparatus, method and program that make it possible for a user to easily recognize courses of diseases for which a patient was examined by doctors during a predetermined period.

A medical information display apparatus of the present invention is a medical information display apparatus comprising:

a timeline display means that displays a timeline representing a time axis on a display device;

a timeline selection input receiving means that receives a selection input selecting a predetermined period on the timeline;

an electronic medical record information retrieval means that obtains a set of pieces of electronic medical record information by retrieving, from an electronic medical record storage means that stores a multiplicity of pieces of electronic medical record information, electronic medical record information about examination and treatment received by a predetermined person to be examined during the selected period;

an examination target region extraction means that extracts all of at least one examined region that is recorded in the set of pieces of electronic medical record information; and an examined-region position display means that displays an external view image representing an external view of the person to be examined on the display device, and superimposes a mark representing each of the extracted all of at least one examined region at a position corresponding to the examined region in the external view image.

An operation method of the medical information display apparatus of the present invention is an operation method comprising the steps of:

displaying, by the timeline display means, the timeline representing a time axis on the display device;

receiving, by the timeline selection input receiving means, a selection input selecting a predetermined period on the timeline;

obtaining, by the electronic medical record information retrieval means, a set of pieces of electronic medical record information by retrieving, from an electronic medical record storage means that stores a multiplicity of pieces of electronic medical record information, electronic medical record information about examination and treatment received by a predetermined person to be examined during the selected period;

extracting, by the examination target region extraction means, all of at least one examined region that is recorded in the set of pieces of electronic medical record information; and displaying, by the examined-region position display means, an external view image representing an external view of the person to be examined on the display device, and superimposing a mark representing each of the extracted all of at least one examined region at a position corresponding to the examined region in the external view image.

A medical information display program of the present invention is a medical information display program for causing a computer to function as:

a timeline display means that displays a timeline representing a time axis on a display device;

a timeline selection input receiving means that receives a selection input selecting a predetermined period on the timeline;

an electronic medical record information retrieval means that obtains a set of pieces of electronic medical record information by retrieving, from an electronic medical record storage means that stores a multiplicity of pieces of electronic medical record information, electronic medical record information about examination and treatment received by a predetermined person to be examined during the selected period;

an examination target region extraction means that extracts all of at least one examined region that is recorded in the set of pieces of electronic medical record information; and an examined-region position display means that displays an external view image representing an external view of the person to be examined on the display device, and superimposes a mark representing each of the extracted all of at least one examined region at a position corresponding to the examined region in the external view image.

The term "external view image" refers to a schematic diagram illustrating an external view of a human body. The external view image represents a standard shape of a head, a chest, an abdomen, an arm, a leg, or the like.

It is desirable that the examined-region position display means obtains the degree of importance of each examined region based on electronic medical record information related to the examined region in the set of pieces of electronic medical record information, and displays the mark representing each examined region in such a manner that the color of the mark representing an examined region having a high degree of importance is intense, and that the color of the mark is less intense as the degree of importance is lower.

The expression "displays the mark representing each examined region in such a manner that the color of the mark representing an examined region having a high degree of importance is intense, and that the color of the mark is less intense as the degree of importance is lower" means that marks representing plural examined regions are displayed in such a manner that the gradation level (pixel or voxel values, density or the like) or the gray level of a mark representing an examined region having a high degree of importance is higher than that of a mark representing an examined region having a low degree of importance, and that the gradation level or the gray level of a mark representing an examined region gradually becomes lower as the degree of importance of the examined region is lower.

Further, the degree of importance of each examined region may be obtained based on at least one of the kind of an organ in the examined region, a disease name of the examined region, the surgery method of a surgery performed on the examined region, the number of times of surgery performed on the examined region, and the frequency of examination performed by a doctor on the examined region.

Further, it is desirable that the medical information display apparatus includes a first instruction input receiving means that receives an instruction input selecting one of the marks displayed on the display device, and a first electronic medical record information display means that displays, based on the instruction input received by the first instruction input receiving means, electronic medical record information related to an examined region corresponding to the selected mark in the set of pieces of electronic medical record information on the display device.

Further, it is desirable that the medical information display apparatus includes an examined region information display means that displays, based on the set of pieces of electronic medical record information, at least one disease name of the examined region represented by each mark displayed on the display device and/or the surgery name of at least one surgery performed on the examined region in the vicinity of the mark, a second instruction input receiving means that receives an instruction input selecting one of the at least one disease name of the examined region and the surgery name of at least one surgery performed on the examined region displayed in the vicinity of the mark, and a second electronic medical record information display means that displays, based on the instruction input received by the second instruction input receiving means, electronic medical record information in the set of pieces of electronic medical record information, and the information being related to the selected disease name or the selected surgery name of a surgery performed on the examined region, on the display device.

Further, it is desirable that the medical information display apparatus includes a medical image display means that retrieves, from a medical image storage means that stores a multiplicity of medical images, a medical image related to the electronic medical record information displayed by the first or second electronic medical record information display means, and displays the retrieved medical image on the display device.

Further, it is desirable that the medical information display apparatus includes an examination information display means that retrieves, from an examination information storage means that stores a multiplicity of pieces of examination information, examination information related to the electronic medical record information displayed by the first or second electronic medical record information display means, and displays the retrieved examination information on the display device.

Further, it is desirable that the timeline selection input receiving means receives an input by one of a mouse, a keyboard and a touch panel provided at the display device.

Since electronic medical record information about examination and treatment received by a person to be examined during a period selected on a timeline is retrieved, and all of at least one examined region that is recorded in the retrieved set of pieces of electronic medical record information is extracted, and a mark representing each of the extracted all of at least one examined region is superimposed on an external view image representing an external view of a human body, it is possible to immediately recognize examined regions for which the person to be examined was examined by a doctor during the selected period.

Further, since a mark representing each examined region is displayed in such a manner that the color of the mark representing an examined region having a high degree of importance is intense, and that the color of a mark is less intense as the degree of importance is lower, it is possible to identify, based on the gradation level (or gray level) of the mark representing the examined region, an organ that had an important disease to be noted.

When one of the marks is selected, electronic medical record information in the set of pieces of electronic medical record information, and the information being related to an examined region corresponding to the selected mark, may be displayed. In such a case, it is possible to identify the course of past treatment for each examined region.

Further, at least one disease name of the examined region represented by each mark and/or the surgery name of at least one surgery performed on the examined region may be displayed in the vicinity of the mark, and when one of the at least one disease name of the examined region represented by each mark and the surgery name of at least one surgery performed on the examined region is selected, electronic medical record information in the set of pieces of electronic medical record information, and the information being related to the selected disease name of the examined region or the selected surgery name of a surgery performed on the examined region, may be displayed. In such a case, even when an examined region had plural diseases, it is possible to identify the course of past treatment, focusing only on a specific disease, or a surgery performed for treatment of the disease.

Further, when a medical image or examination information related to displayed electronic medical record information is also displayed, it is possible to recognize and observe the whole operation performed on a patient, such as various kinds of image-based diagnosis and results of examination.

BEST MODE FOR CARRYING OUT THE INVENTION

Figure 1:
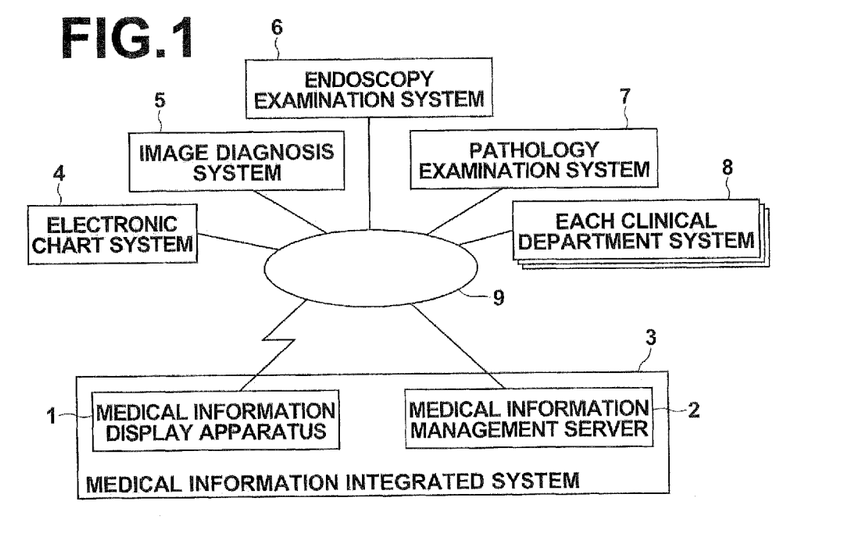
FIG. 1 is a diagram illustrating the configuration of a medical information integrated system including a medical information display apparatus according to an embodiment of the present invention and peripheral systems of the system.

FIG. 1 is a diagram illustrating a medical information integrated system 3 including a medical information display apparatus 1 according to an embodiment of the present invention and peripheral systems of the system. As illustrated in FIG. 1, the medical information management system 3 is connected to an electronic chart system 4, an image diagnosis system 5, an endoscopy examination system 6, a pathology examination system 7, and each clinical department system 8 through a network 9. Further, the medical information integrated system 3 includes the medical information display apparatus 1 according an embodiment of the present invention and a medical information management server 2.

In the present embodiment, medical information generated at the electronic chart system 4, the image diagnosis system 5, the endoscopy examination system 6, the pathology examination system 7, and each clinical department system 8 is managed by the medical information management server 2 in an integrated manner. Further, the medical information display apparatus 1 requests medical information from the medical information management server 2, and displays the medical information matching the request, which has been provided by the medical information management server 2.

The medical information display apparatus 1 is a computer, such as a workstation. The medical information display apparatus 1 includes known hardware elements, such as a CPU, a main storage device, an auxiliary storage device, an input/output interface, a communication interface, an input device (a mouse, a keyboard, or the like), a display device (a display monitor, a liquid crystal display, or the like), and a data bus. Further, a known operating system and the like have been installed in the medical information display apparatus 1. It is desirable that a touch panel is provided at the display device so that an input by a finger operation is possible in combination with GUI.

As the touch panel, a known touch panel using a resistive film, capacitance, electromagnetic induction, surface elastic wave (ultrasonic wave), infrared rays or the like may be used. However, it is desirable that the touch panel is a projected capacitance touch panel or the like, which can detect multiple touches (touches at plural positions), so that various finger operations are detectable.

Figure 2:
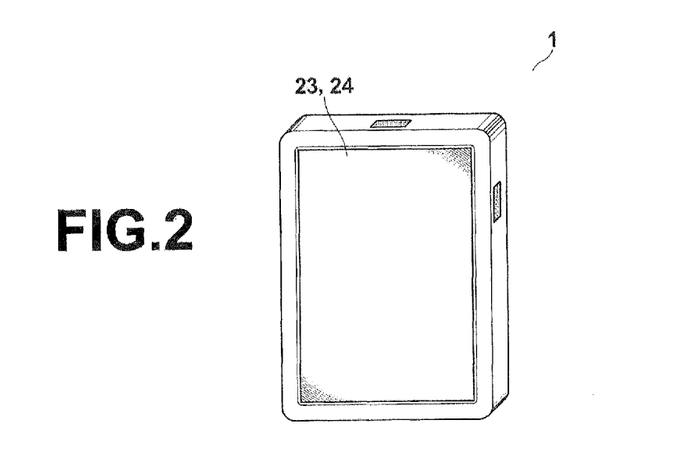
FIG. 2 is a diagram illustrating an example of an external view of a medical information display apparatus according to an embodiment of the present invention.

The medical information display apparatus 1 may be a tablet-type terminal, as illustrated in FIG. 2, including a touch panel 23 and a liquid crystal display 24 that are formed, in an integrated manner, on the front side of the touch panel 23. The tablet-type terminal is a portable computer. Further, communication between the medical information display apparatus 1 and the medical information management server 2 is performed through a known mobile communication network, a wireless LAN, or the like.

Meanwhile, the medical information management server 2 is a computer including a medical information database. A known operating system, software for managing a database, application software for registering medical information in the medical information database or extracting medical information from the database, and the like are installed in the medical information management server 2.

The electronic chart system 4 is a known computer system. For example, a terminal at each clinical department or the like and an electronic chart management server 41 including an electronic chart database are connected to each other through the network 9 in such a manner that they can communicate with each other. Electronic medical record information (electronic health record information) (hereinafter, referred to as electronic chart information) is stored in the electronic chart database. Electronic chart information that has been input at a terminal of each clinical department or the like is managed by using the electronic chart database.

The electronic chart information includes, for example, patient's information including a patient's name, the date of birth, sex and the like, examined-region information, examination order information including dates of various kinds of examination, the content of instruction for examination and the like, diagnosis information including the date of examination by a doctor, a chief complaint, a definite diagnosis name and the like, treatment information including the date of a surgery, treatment, drug administration or the like, and the content of treatment, and the like. The electronic chart database has a database structure in which a patient's ID for identifying each patient is correlated with the electronic chart information.

Various kinds of examination include examination performed at an examination room away from each clinical department based on examination order information issued by each clinical department, and examination, such as electrocardiogram, performed at each clinical department. The examination performed at the examination room includes endoscopy examination, pathology examination and image-based diagnosis. Further, an examination type and the content of examination are recorded, in detail, in the examination order information. Medical images obtained by imaging based on the examination order information, and examination information including the result of examination performed based on the examination order information are managed by the image diagnosis system 5, the endoscopy examination system 6, the pathology examination system 7 or the like. Further, examination information, such as a result of examination performed at each clinical department, is managed by each clinical department system 8.

Further, the image diagnosis system 5 is a known computer system. For example, the image diagnosis system 5 includes a workstation of a doctor who is in charge of image-based diagnosis (image interpretation, image reading, or the like), an image management server 51 including an image database in which image data obtained by imaging at a modality, such as CT and MRI, are stored, and an image interpretation report server 52 including an image interpretation report database in which a result of image interpretation with respect to an image obtained by imaging is stored, which are connected to each other through the network 9 in such a manner that they can communicate with each other. Here, the workstation of a doctor in charge of image interpretation can perform, based on a purpose and a target of diagnosis, known image processing, such as MIP, MPR, CPR and volume rendering (VR), and known image analysis processing, such as bone extraction or removal, blood vessel extraction, organ extraction and abnormal shadow detection, in combination. Further, image data after such processing and analysis are also stored in the image database. The image data include both of two-dimensional images (pixel data) and three-dimensional image (voxel data), and both of static images and video images (motion or dynamic images). Further, the image database stores a patient's ID and supplementary information, such as an image ID for identifying each image, information about a modality used to obtain the image and information about a region of a person to be examined represented in the image, in such a manner that they are correlated with the image. The information about a modality is given when the image is generated at the modality. Meanwhile, the information about a region of a person to be examined may be given based on an examination order or the like when the image is generated at the modality. Alternatively, if the image is a tomographic image of CT or the like, such information may be given for each slice at the workstation of a doctor in charge of image interpretation by using a known region recognition processing method (for example, please refer to Japanese Unexamined Patent Publication No. 2008-259682, or the like). Further, the image interpretation report database has a database structure in which an image interpretation report, a patient's ID and an image ID of target image data of image interpretation are correlated with each other. The image data and the image interpretation report may be indirectly correlated with a patient's ID through examination order information that identifies each examination (imaging).

Further, the endoscopy examination system 6 is a known system. An endoscopy examination management server 61 including an endoscopy examination database controls access to the endoscopy examination database. The endoscopy examination database stores real endoscopy image data obtained by imaging by various kinds of endoscope, endoscopy examination reports summarizing results of endoscopy examination and the like in such a manner that they are correlated with examination order information and patients' ID's.

Further, the pathology examination system 7 is a known system. A pathology examination management server 71 including a pathology examination database controls access to the pathology examination database. The pathology examination database stores microscope image data obtained by pathology examination, pathology examination reports summarizing results of pathology examination and the like in such a manner that they are correlated with examination order information and patients' ID's.

In each clinical department system 8, a clinical department examination management server 81 including a database of each clinical department controls access to the database of the clinical department. The database of each clinical department stores examination data obtained by examination at the clinical department, examination reports and the like in such a manner that they are correlated with examination order information and patients' ID's. For example, the examination data obtained by examination at the clinical department are electrocardiogram data or the like (waveform, numerical values or the like) if the clinical department is a vascular department of a hospital. The examination data obtained by examination at the clinical department are hearing examination data or the like (waveform, numerical values or the like) if the clinical department is an otolaryngology department. The examination data obtained by examination at the clinical department are eye test data, fundus examination data or the like (numerical values or the like) if the clinical department is an ophthalmology department.

In the present embodiment, a case in which medical information based on a request sent from the medical information display apparatus 1 is obtained from the medical information management server 2, and the obtained medical information is displayed at a display device of the medical information display apparatus 1 will be described. In the present embodiment, the medical image includes image data obtained by imaging at a modality, image data after image processing, real endoscopy image data, and microscope image data. Further, the examination information includes an image interpretation report, an endoscopy examination report, a pathology examination report, electrocardiogram data (waveform, numerical values or the like), hearing examination data (waveform, numerical values or the like), eye test data, fundus examination data, and the like. In the following descriptions, it is assumed that an image management server 51, an endoscopy examination management server 61 and a pathology examination management server 71 constitute a medical image storage means of the present invention, and that the endoscopy examination management server 61, an image interpretation report server 52, a pathology examination management server 71 and each clinical department examination management server 81 constitute an examination information storage means of the present invention.

Figure 3:
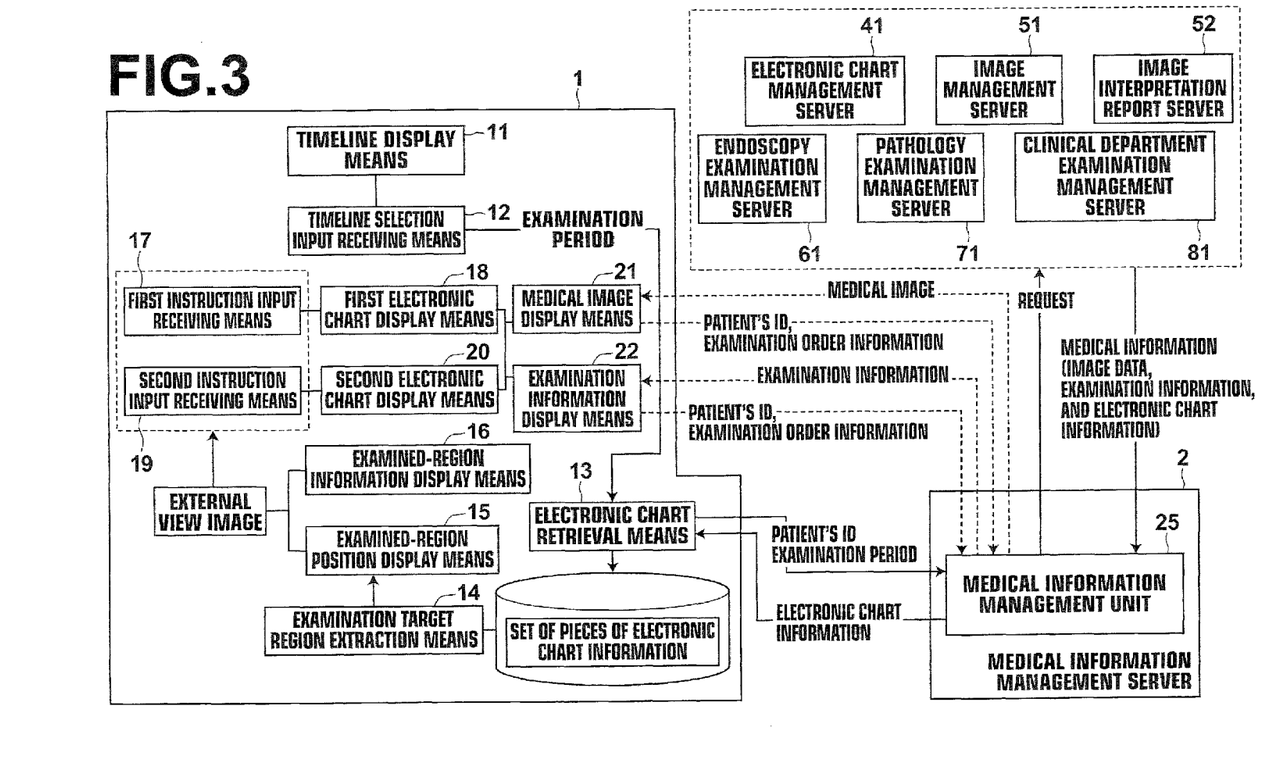
FIG. 3 is a block diagram illustrating major composition elements of a medical information display apparatus according to an embodiment of the present invention and a medical information management server.

FIG. 3 is a schematic block diagram illustrating functions provided in the medical information display apparatus 1 and the medical information management server 2. As illustrated in FIG. 3, the medical information display apparatus 1 of the present invention includes a timeline display means 11, a timeline selection input receiving means 12, an electronic chart retrieval means (electronic medical record information retrieval means) 13, an examination target region extraction means 14, an examined region position display means 15, an examined region information display means 16, a first instruction input receiving means 17, a first electronic chart display means (first electronic medical record information display means) 18, a second instruction input receiving means 19, a second electronic chart display means (second electronic medical record information display means) 20, a medical image display means 21, and an examination information display means 22. Further, a medical information management unit 25 in the medical information management server 2 manages, based on patients' ID's, the location of medical information generated in different systems (the different systems mean the electronic chart system 4, the image diagnosis system 5, the endoscopy examination system 6, the pathology examination system 7, and each clinical department system 8). Further, the medical information management unit 25 requests and obtains medical information from servers of other systems.

Figure 4A:
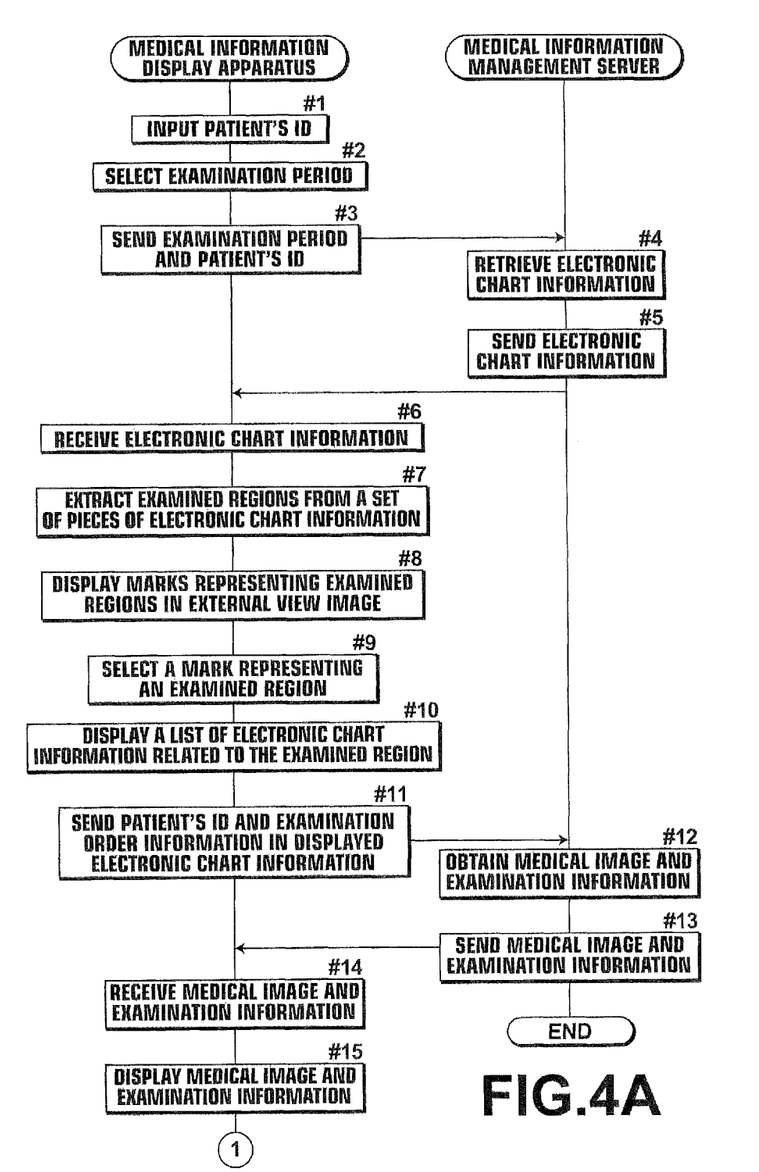
FIG. 4A is a flow chart (No. 1) illustrating a flow of processing for displaying medical information performed in the medical information integrated system.
Figure 4B:
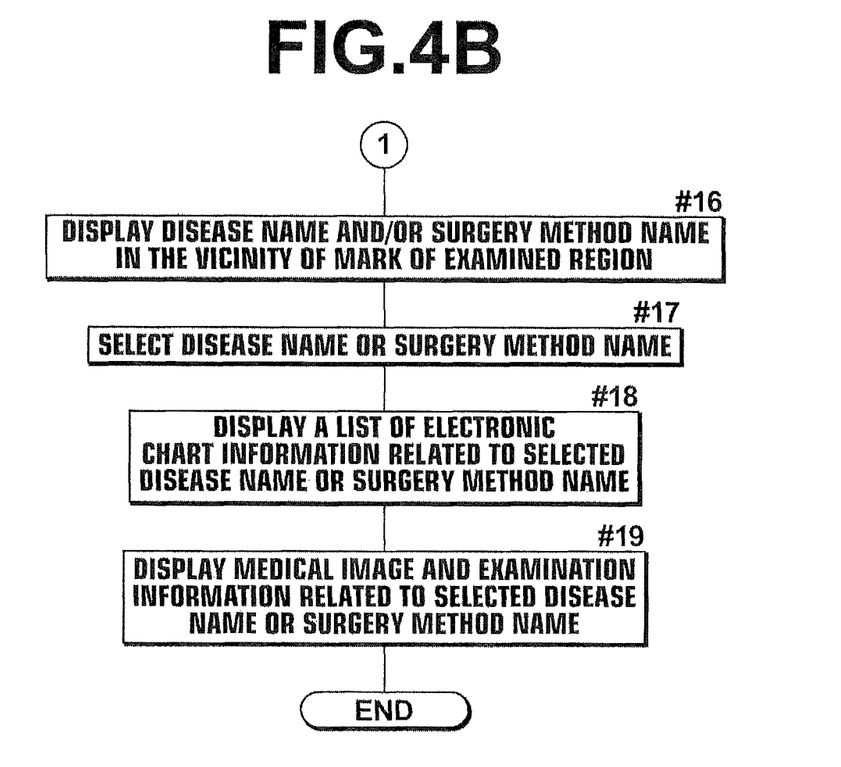
FIG. 4B is a flow chart (No. 2) illustrating a flow of processing for displaying medical information performed in the medical information integrated system.
Figure 5:
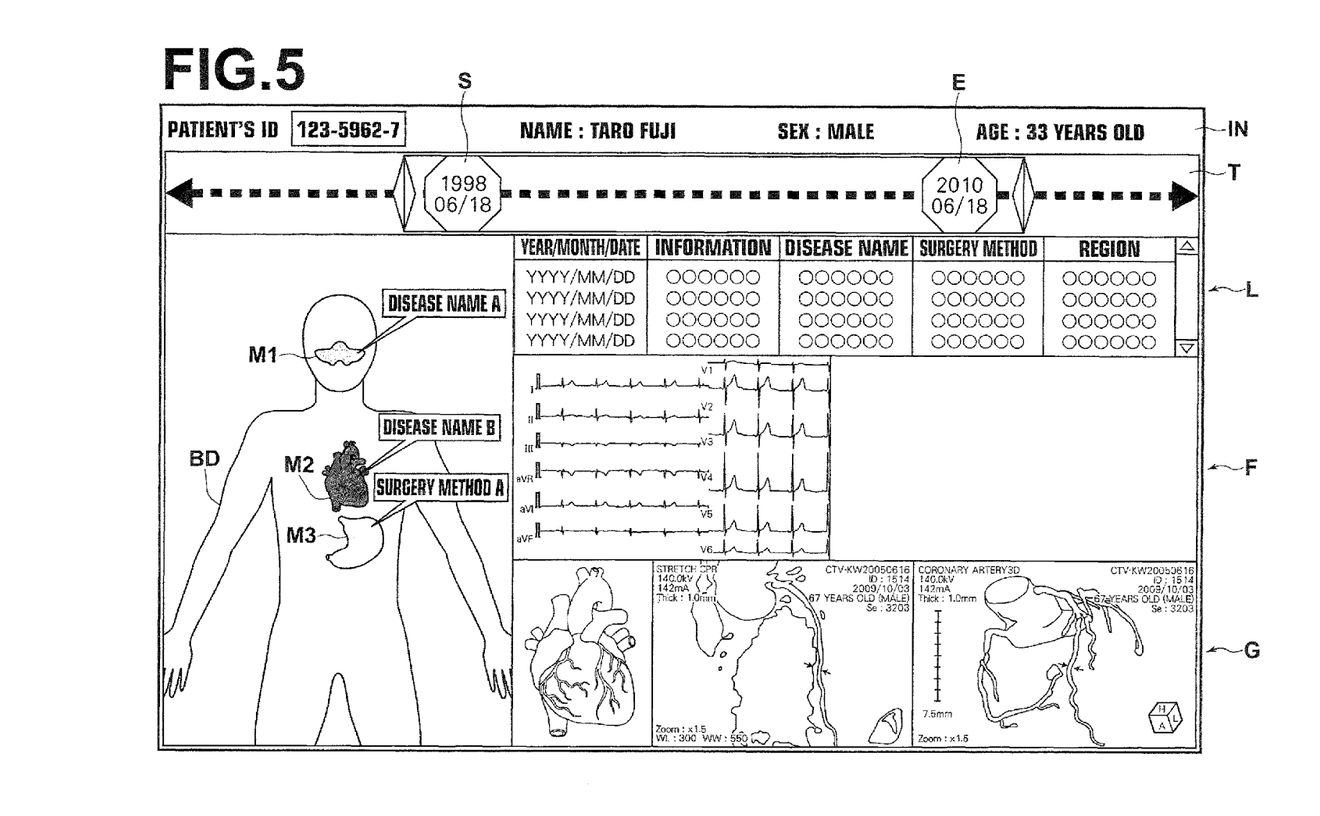
FIG. 5 is a diagram illustrating an example of a display screen that displays an external view image of a human body and a list of medical information.

FIGS. 4A and 4B are flow charts illustrating a flow of processing performed in the medical information integrated system 3. FIG. 5 is a diagram illustrating an example of a display screen of a display device in the medical information display apparatus 1.

With reference to FIGS. 3, 4A, 4B and 5, the flow of whole medical information display processing will be described together with each processing of the medical information display apparatus 1. Further, the content of each processing performed by the medical information management unit 25 in the medical information management server 2 will be described.

First, as illustrated in FIG. 5, the medical information display apparatus 1 displays input section IN of a patient's ID on a display screen of a display device. A user inputs a patient's ID in the input section IN by using a keyboard (step #1).

Then, the timeline display means 11 displays timeline T representing a time axis at an upper part of the display screen of the display device.

The timeline selection input receiving means 12 receives an input of an examination period (a time period of examination, treatment or the like) that is selected on the timeline displayed at the display device. For example, when a user wants to check electronic chart information about diseases of a patient approximately in the past 12 years, the user sets mark S indicating a start time of the examination period at the position of Jun. 18, 1998 ("1998 06/18") on the timeline T in the display screen by using a mouse. Further, the user places mark E indicating an end time of the examination period at the position of Jun. 18, 2010 ("2010 06/18"), and performs an operation to determine the examination period. Then, the timeline selection input receiving means 12 receives the period of from Jun. 18, 1998 through Jun. 18, 2010, as an examination period (step #2). It is not necessary that the period is input by the mouse. Alternatively, the timeline selection input receiving means 12 may receive an input of an examination period by an operation using a touch panel provided at the display device or a keyboard.

Next, the electronic chart retrieval means 13 sends the examination period and a patient's ID to the medical information management server 2, and requests electronic chart information about examination and treatment performed on a patient identified by the patient's ID during the selected examination period (step #3). Based on this request, the patient ID and the selected examination period are transferred from the medical information management server 2 to the electronic chart management server 41 of the electronic chart system 4. Further, all of at least one piece of electronic chart information that matches the patient's ID, and that represents information with the date of examination by a doctor within the examination period is retrieved from the electronic chart management server 41 (step #4). The retrieved set of pieces of electronic chart information is sent from the electronic chart management server 41 to the medical information display apparatus 1 through the medical information management server 2 (step #5). The medical information display apparatus 1 stores the received set of pieces of electronic chart information temporarily in an auxiliary storage device (step #6).

Then, the examination target region extraction means 14 extracts all of at least one examined region from examined region information recorded in the set of pieces of electronic chart information, which is stored in the auxiliary storage device of the medical information display apparatus 1 (step #7). In some cases, a patient is examined for plural organs, such as the heart and the liver, during an examination period. In such a case, one or more examined regions are extracted from the set of pieces of electronic chart information.

The examined region position display means 15 displays external view image BD representing an external view of a human body (a person to be examined) at the display device, and displays marks M1, M2 and M3 representing examined regions that have been extracted by the examination target region extraction means 14 in such a manner that the marks M1, M2 and M3 are superimposed on the external view image BD (step #8). It is desirable that marks M1, M2 and M3 of examined regions are icons of organs schematically illustrating the respective organs, as illustrated in FIG. 5, so that a user can immediately identify an organ represented by each icon. The icons of organs are superimposed on the external view image BD at positions corresponding to respective organs in the human body. Further, marks M1, M2 and M3 of examined regions are displayed, based on the degrees of importance of respective examined regions, in such a manner that the marks M1, M2 and M3 with high degrees of importance are displayed in intense colors, and that the colors of the marks M1, M2 and M3 are less intense as the degrees of importance are lower. Alternatively, the marks may be displayed in different colors based on the degrees of importance. For example, a mark having a high degree of importance may be displayed in red, and a mark having a low degree of importance may be displayed in yellow.

The set of pieces of electronic chart information stored in the auxiliary storage device is classified into examined regions, and the degree of importance of each of the examined regions is obtained based on information stored in electronic chart information related to the respective examined regions. For example, if an examined region is an important organ, such as the heart and the brain, the degree of importance of the examined region is judged to be high. Further, even if the examined region is the same, the degree of importance of a disease differs depending on a disease name and the kind of a surgery performed on the examined region. Further, it is recognized that the degree of importance is higher, as the number of times of surgery is larger and the frequency of examination by a doctor is higher. Therefore, the degree of importance of each examined region is obtained in the following manner. Accumulated past electronic chart information and information written on paper charts are analyzed, and the degree of importance of each examined region is determined by using factors, such as the kind of an organ in the examined region, a disease name of the examined region, the surgery method of a surgery performed on the examined region, the number of times of surgery, and the frequency of examination by a doctor with respect to the examined region, in combination. An importance degree table showing a relationship between each factor and the degree of importance is generated in advance, and each factor is extracted from information recorded in electronic chart information related to each examined region. Further, the degree of importance of the examined region is obtained based on the importance degree table.

As described above, marks M1, M2, M3 representing organs in examined regions are superimposed on external view image BD displayed on the display screen of the display device. Therefore, the user can identify which organs were examined in the past, in other words, which organs are examined regions by referring to marks M1, M2 and M2 representing the examined regions displayed on the display screen. Further, the user can identify, based on gradation levels or gray levels (or colors) of marks M1, M2 and M3 representing examined regions, whether organs had important diseases to be noted.

Further, a user wants to check the content of electronic chart information in detail especially with respect to a region of interest among the past examined regions. Therefore, a GUI is provided so that the user can check electronic chart information related to each examined region separately.

The user clicks one of marks M1, M2 and M3 of examined regions displayed on the external view image BD by using a mouse when the user wants to check electronic chart information about the one of marks M1, M2 and M3. For example, mark M2 of the heart is clicked. Then, the first instruction input receiving means 17 receives information representing that the selected examined region is the heart (step #9).

The first electronic chart display means 18 retrieves, from the set of pieces of electronic chart information stored in the auxiliary storage device, electronic chart information related to the examined region (the heart in this case) received by the first instruction input receiving means 17, and displays list L of the retrieved electronic chart information on the right side of the display screen, in which the external view image BD is displayed, as illustrated in FIG. 5 (step #10). Then, the user performs, by using a mouse, a touch panel or the like, an operation for selecting a section or the like of electronic chart information in the list L of the electronic chart information when the user wants to check the content of the electronic chart information in detail. When an input of the operation is received by the first electronic chart display means 18, the first electronic chart display means 18 displays diagnosis information, such as a chief complaint and a definite diagnosis name, and treatment information, such as the date of a surgery, treatment, drug administration or the like, and the content of treatment, and the like that are recorded in the selected electronic chart information.

When results of various kinds of examination performed to diagnose a patient are displayed together with the list of electronic chart information, it is possible to recognize and observe the whole examination performed on the examined region.

Therefore, the medical image display means 21 and the examination information display means 22 display a medical image and examination information related to the electronic chart information displayed as a list by the first electronic chart display means 18.

First, a patient's ID and examination order information are extracted from the electronic chart information displayed, as a list, by the first electronic chart display means 18. The patient's ID and the examination order information are sent to the medical information management server 2 to request a medical image and examination information (step #11). When the examination order information represents imaging by a modality, such as CT and MRI, the medical information management server 2 transfers the patient's ID and the examination order information to the image management server 51, and obtains a medical image corresponding to the patient's ID and the examination order information (step #12). The data obtained from the image management server 51 are not limited to image data obtained by imaging by each modality. Image data on which image processing, such as MIP, MPR, CPR, and volume rendering (VR), has been performed at a work station of a doctor in charge of image-based diagnosis are also obtained from the image management server 51. The patient's ID and the examination order information are transferred also to the image interpretation report server 52, and an image interpretation report related to the medical image obtained from the image management server 51 is obtained from the image interpretation report server 52. The obtained medical image and image interpretation report are transferred to the medical information display apparatus 1 through the medical information management server 2 (step #13). Further, the image data and the image interpretation report received by the medical information display apparatus 1 are temporarily stored in the auxiliary storage device (step #14).

Similarly, when real endoscopy image data obtained by endoscopy examination and an endoscopy examination report, microscope image data obtained by pathology examination and a pathology examination report, examination data about examination performed at each clinical department, such as an electrocardiogram, or the like are obtained, processing is performed in the following manner. The medical information management server 2 transfers, based on the type of examination in the examination order information, the patient's ID and the examination order information to a server corresponding to the type of examination among the endoscopy examination management server 61, the pathology examination management server 71, and the clinical department examination management server 81. Accordingly, the medical information management server 2 obtains a medical image and examination information corresponding to a request from the server 61, 71 or 81 (step #12). The obtained medical image and examination information are sent from the server 61, 71 or 81 to the medical information display apparatus 1 through the medical information management server 2 (step #3). The medical image and the examination information received by the medical information display apparatus 1 are temporarily stored in the auxiliary storage device (step #14).

The medical image display means 21 displays the medical image stored in the auxiliary storage device of the medical information display apparatus 1. The medical image is displayed on right side G of the external view image BD, in which the marks M1, M2 and M3 of examined regions are displayed. Further, the examination information display means 22 displays the examination information stored in the auxiliary storage device of the medical information display apparatus 1 on right side F of the external view image BD, in which the marks M1, M2 and M3 of examined regions are displayed (step #15).

For example, when the examined region received by the first instruction input receiving means 17 is the heart, image data, such as a CT image of the heart, a CPR image of a coronary artery, and a VR image of the heart, are obtained from the image management server 51. Further, an image interpretation report about the aforementioned image is obtained from the image interpretation report server 52, and electrocardiogram data are obtained from the clinical department examination management server 81 in a vascular department. The obtained image data, image interpretation report and electrocardiogram data are displayed on the right side of a display screen of the display device in the medical information display apparatus 1.

As illustrated in FIG. 5, medical images and examination information are converted into reduced images and arranged on a display screen so that they are observable, as a list, on the same display screen. It is desirable that medical images and examination information are classified, based on the kind of a modality used in imaging and the kind of examination, in such a manner that the same kind of medical images or examination information is displayed on the same row or the like. Further, the display screen is structured in such a manner that it is possible to check information about each image and examination data in detail by clicking a reduced image of each image and examination information by a mouse.

Further, the examined region information display means 16 retrieves, from electronic chart information related to each examined region in the set of pieces of electronic chart information stored in the auxiliary storage device, a disease name of each examined region or the name of the surgery method of a surgery performed on the examined region. Further, the examined region information display means 16 displays the disease name of the examined region or the name of the surgery method of a surgery performed on the examined region in the vicinity of each of marks M1, M2 and M3 displayed on the display device (please refer to FIG. 5) (step #16). When plural disease names are retrieved, or when both of a disease name and the name of a surgery method are retrieved, all of the retrieved disease names and the name of a surgery method are displayed on a side of each of the marks M1, M2 and M2 of the examined regions. The disease name and the name of the surgery method may be displayed in such a manner that they are displayed only when a mouse is placed on the marks M1, M2 and M2 of the examined regions.

Further, a user wants to check the content of electronic chart information in detail, especially, with respect to a disease to be noted and a surgery to be noted among organs displayed with marks M1, M2 and M3 of examined regions. Therefore, a GUI is provided so that the user can check electronic chart information related to each disease or each surgery method separately.

When the user performs an operation for selecting one of a disease name and the name of a surgery method by using a mouse (step #17), the second instruction input receiving means 19 receives information representing selection of the disease name or the name of a surgery method.

The second electronic chart display means 20 retrieves, from the set of pieces of electronic chart information stored in the auxiliary storage device, electronic chart information related to the selected disease name or the selected name of a surgery method. Further, the second electronic chart display means 20 displays list L of the retrieved electronic chart information on the right side of the display screen in which marks M1, M2 and M3 of examined regions are displayed on the external view image BD (step #18). The user performs, by using a mouse or a touch panel, an operation for selecting a section or the like of electronic chart information in the list L of electronic chart information when the user wants to check the content of the electronic chart information in the section or the like in detail. Then, the second electronic chart display means 20 receives the input operation, and displays diagnosis information, such as a chief complaint and a definite diagnosis name, and treatment information, such as the date of a surgery, treatment, drug administration or the like, and the content of treatment, and the like that are recorded in the selected electronic chart information.

The medical image display means 21 and the examination information display means 22 display a medical image and examination information related to the electronic chart information displayed as a list by the second electronic chart display means 20. Meanwhile, medical images and examination information related to the electronic chart information about examined regions displayed as a list by the first electronic chart display means 18 have been stored in the auxiliary storage device of the medical image display apparatus 1. Therefore, a medical image and examination information related to the electronic chart information (i.e., a disease name and the name of a surgery method) displayed as a list by the second electronic chart display means 20 are retrieved from the auxiliary storage device. Further, reduced images of the retrieved medical image and examination information are displayed on right side F and G of the display screen in which marks M1, M2 and M3 of examined regions are displayed on the external view image BD (step #19).

The user repeats an operation for selecting an examined region (first instruction input receiving means 17) and an operation for selecting a disease name or the name of a surgery method (second instruction input receiving means 19) to display a list of electronic chart information necessary for diagnosis. Display of the electronic chart information is switched several times, based on the operations by the user, between display of a list of electronic chart information corresponding to an examined region and display of a list of electronic chart information corresponding to a disease name or the name of a surgery method. Further, the medical image and examination information displayed as a list by the medical image display means 21 and the examination information display means 22 are also switched several times between display of a list corresponding to an examined region and display of a list corresponding to a disease name or the name of a surgery method. When the display is switched, if the medical image and examination information corresponding to the examination order information in the electronic chart information displayed as a list have been already obtained from each of the servers 51, 52, 61, 71 and 81, and stored in the auxiliary storage device, the medical image and the examination information may be retrieved from the auxiliary storage device, without requesting the medical image and the examination information from the medical information management server 2. Further, the medical image and the examination information that are retrieved from the auxiliary storage device are displayed. In contrast, if the medical image and examination information corresponding to the examination order information in the electronic chart information displayed as a list are not present in the auxiliary storage device of the medical image display apparatus 1, the medical image and the examination information may be requested by sending the patient's ID and the examination order information to the medical information management server 2. The medical image and the examination information based on the request are obtained from each of the servers 51, 52, 61, 71 and 81 through the medical information management server 2. Further, the obtained medical image and examination information are displayed.

As described above in detail, with respect to regions examined during an examination period selected on timeline T, marks of the examined regions are displayed on an external view image of a human body. Further, electronic chart information, a medical image, and examination information for each examined region are displayed in such a manner that they are observable as a list. Therefore, a user can instinctively recognize what kind of disease each examined region had. Further, if the electronic chart information, the medical image and the examination information are displayed as a list for each disease name/the name of each surgery method, it is possible to easily recognize the outline of the course of each disease and the course of conditions each surgery.

In the aforementioned embodiment, a case of displaying the electronic chart information, the medical image and the examination information as a list for each examined region or for each disease name/the name of each surgery method was described. Alternatively, all of electronic chart information, medical images and examination information in a selected examination period may be displayed, as a list, first.

When many medical images and many pieces of examination information to be displayed as a list are detected, it is desirable that the medical images and examination information are displayed as reduced images by classifying them into separate sections or the like based on each information, such as a disease name, an examined region, a modality, and a surgery method.

In the aforementioned embodiment, the medical information management server 2 that manages medical information in an integrated manner is provided. Further, the medical information display apparatus 1 obtains medical information through the medical information management server 2. Alternatively, the medical information may be obtained directly from each of other systems, such as the electronic chart system 4, the image diagnosis system 5, the endoscopy examination system 6, the pathology examination system 7, and each clinical department system 8.

Further, in the aforementioned embodiment, a case in which real data of medical information are stored in other systems, such as the electronic chart system 4, the image diagnosis system 5, the endoscopy examination system 6, the pathology examination system 7 and each clinical department system 8, and in which databases of the other systems are used through the medical information management server 2, was described. Alternatively, the real data may be managed at the medical information management server 2 in a centralized manner.

Figure 6:
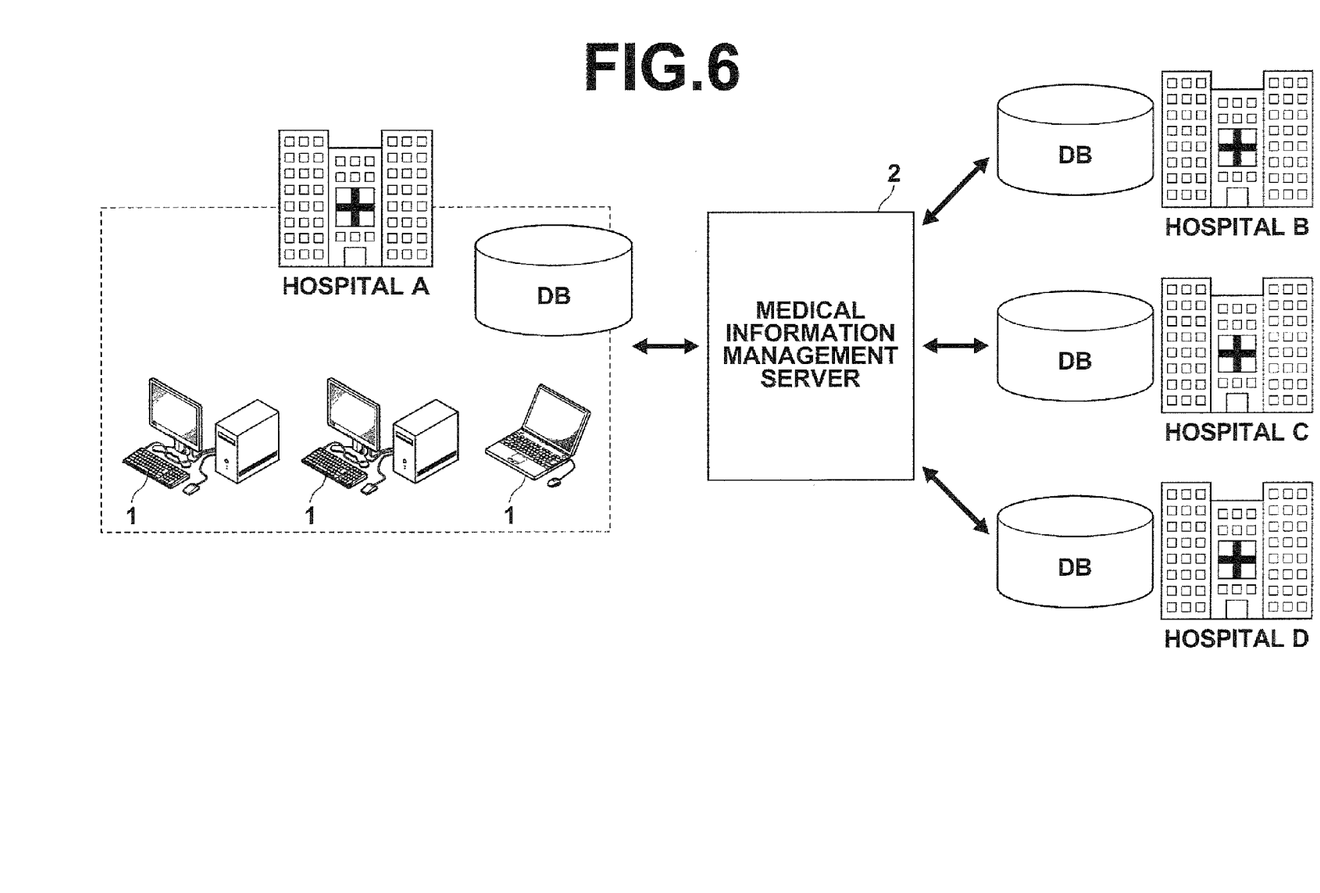
FIG. 6 is a diagram illustrating the configuration of a medical information management system according to the present invention when patient's medical information scattered in different medical institutions is managed in an integrated manner.

In the aforementioned embodiment, a case in which plural systems, such as the electronic chart system 4, the image diagnosis system 5, the endoscopy examination system 6, the pathology examination system 7, and each clinical department system 8, which are provided in the same medical institution, are managed in an integrated mariner was described. Further, as illustrated in FIG. 6, when medical information about a patient is scattered in a medical institution (hospital A) and other medical institutions (hospital B, hospital C and hospital D) located in the same area as the medical institution (hospital A), the medical information management server 2 may manage the scattered medical information in an integrated manner. For that purpose, link information showing correspondence of patients' numbers (patients' ID's) between different medical institutions, and a right to access medical information managed by each medical institution should be managed. Then, it becomes possible to collectively refer to medical information about a patient who has been examined at plural medical institutions, and such information is beneficial to future treatment on the patient.

Figure 7:
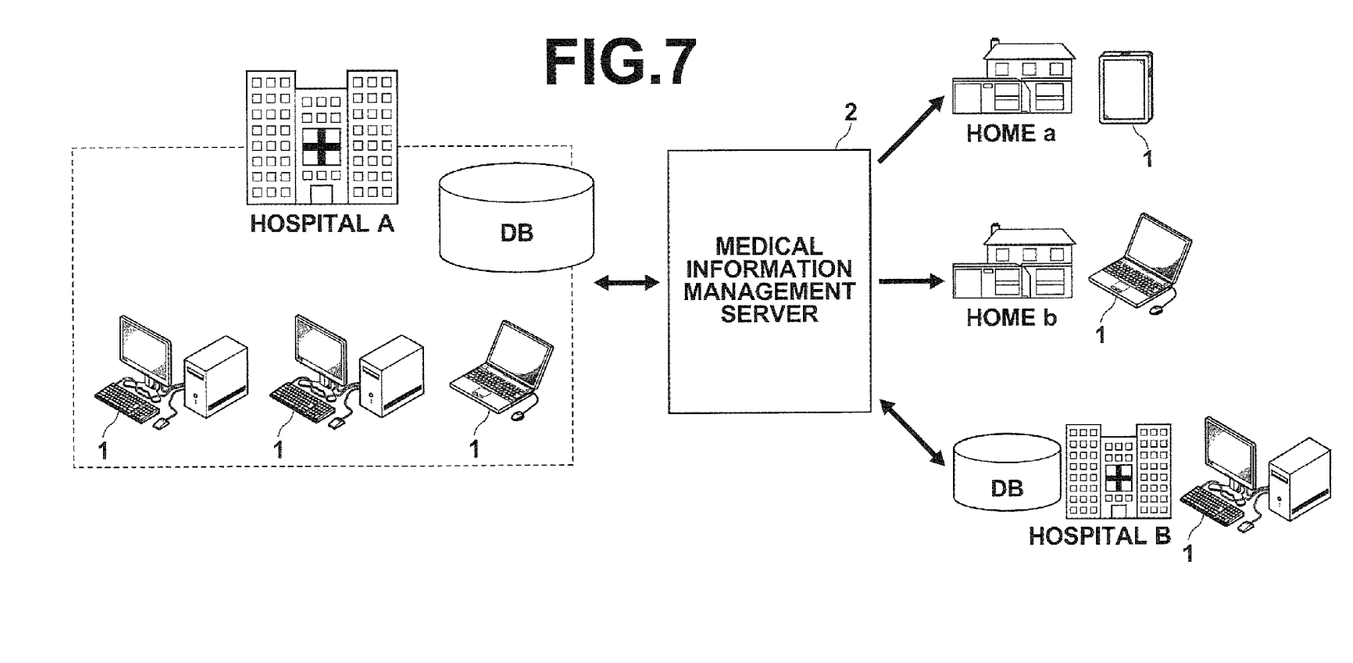
FIG. 7 is a diagram illustrating the configuration of a medical information management system according to the present invention when a user accesses the system from a patient's home.
Figure 8:
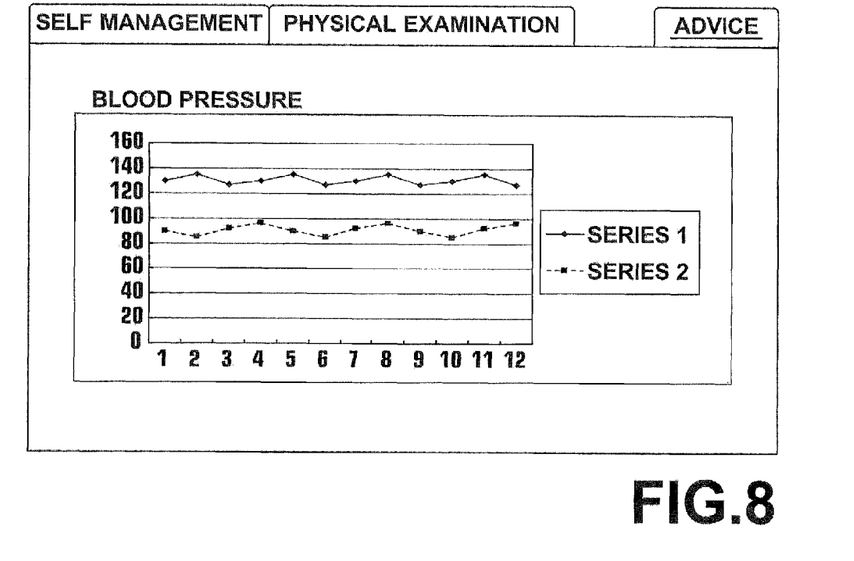
FIG. 8 is a diagram illustrating an example of a display screen in which health condition information managed at a personal computer of a patient's home is displayed.

Further, as illustrated in FIG. 7, a computer, such as a game machine, a tablet-type terminal and a personal computer, with a communication function provided not only at a medical institution but at home a or b of each patient may function as the medical information display apparatus 1. Further, the computer at the patient's home may access the medical information management server 2. When the system is structured in such a manner, it is possible to obtain medical information about examination received at a medical institution also from the patient's home. Further, if health condition information related to the health condition of a patient obtained based on data managed by the patient at home, such as weight, blood pressure, a blood sugar level, and data of a pedometer (registered trademark), is accumulated at an apparatus in the patient's home, it is possible to compare the accumulated information with the medical information about examination received at the medical institution. Specifically, as illustrated in FIG. 8, tab browser "SELF MANAGEMENT" for displaying health condition information and tab browser "PHYSICAL EXAMINATION" for displaying medical information obtained at a medical institution are prepared so that a health condition information display screen (SELF MANAGEMENT) and a medical information display screen (PHYSICAL EXAMINATION) are displayed in separate screens.

Further, advice information related to the health condition information and the medical information may be prepared. For example, when the value of cholesterol of a person extremely exceeds an upper limit of an acceptable range, and the person is at risk of cerebral infarction, if the "advice" button is pressed, the following advice information is displayed:

"Please go to an emergency hospital or call an ambulance when any warning sign of cerebral infarction is observed".

Further, as specific examples of the warning sign of cerebral infarction, the following information related to the symptom of cerebral infarction is displayed on the display screen:

"1. Walk: loss of balance;
2. Talk: trouble speaking;
3. Stretch hands: weakness of a hand on one side;
4. Look: loss of a part of visual field; and
5. Feel: severe headache".

When a person is dieting and managing his/her weight based on health condition information, if an increase of the weight is detected after reduction of the weight, advice information "Your weight is rebounding. Moderate exercise is recommended because overweight is harmful to your health" is displayed.

As described above, medical information about examination received at a medical institution is obtainable from a patient's home. Further, it is possible to check health condition information managed at a patient's home. Therefore, the patient can recognize his/her current health condition.

What is claimed is:

1. A medical information display apparatus comprising:
a timeline display means that displays a timeline representing a time axis on a display device;
a timeline selection input receiving means that receives a selection input selecting a predetermined period on the timeline;
an electronic medical record information retrieval means that obtains a set of pieces of electronic medical record information by retrieving, from an electronic medical record storage means that stores a multiplicity of pieces of electronic medical record information, electronic medical record information about examination and treatment received by a predetermined person to be examined during the selected period;
an examination target region extraction means that extracts all of at least one examined region that is recorded in the set of pieces of electronic medical record information; and
an examined-region position display means that displays an external view image representing an external view of a human body on the display device, and superimposes one or more marks, each of which represents each of the extracted all of at least one examined region, at one or more positions corresponding to the examined region in the external view image, wherein the timeline selection input receiving means receives the selection of the predetermined period by setting a mark indicating a start time of the examination period and a mark indicating an end time of the examination period on the timeline.

2. A medical information display apparatus, as defined in claim 1, wherein the examined-region position display means obtains the degree of importance of each examined region based on electronic medical record information related to the examined region in the set of pieces of electronic medical record information, and displays the mark representing each examined region in such a manner that the color of the mark representing an examined region having a high degree of importance is intense, and that the color of the mark is less intense as the degree of importance is lower.

3. A medical information display apparatus, as defined in claim 2, wherein the degree of importance of each examined region is obtained based on at least one of the kind of an organ in the examined region, a disease name of the examined region, the surgery method of a surgery performed on the examined region, the number of times of surgery performed on the examined region, and the frequency of examination performed by a doctor on the examined region.

4. A medical information display apparatus, as defined in claim 1, the apparatus further comprising:
   a first instruction input receiving means that receives an instruction input selecting one of the marks displayed on the display device; and
   a first electronic medical record information display means that displays, based on the instruction input received by the first instruction input receiving means, electronic medical record information related to an examined region corresponding to the selected mark in the set of pieces of electronic medical record information on the display device.

5. A medical information display apparatus, as defined in claim 1, the apparatus further comprising:
   an examined region information display means that displays, based on the set of pieces of electronic medical record information, at least one disease name of the examined region represented by each mark displayed on the display device and/or the surgery name of at least one surgery performed on the examined region in the vicinity of the mark;
   a second instruction input receiving means that receives an instruction input selecting one of the at least one disease name of the examined region and the surgery name of at least one surgery performed on the examined region displayed in the vicinity of the mark; and
   a second electronic medical record information display means that displays, based on the instruction input received by the second instruction input receiving means, electronic medical record information in the set of pieces of electronic medical record information, and the information being related to the selected disease name or the selected surgery name of a surgery performed on the examined region, on the display device.

6. A medical information display apparatus, as defined in claim 4, the apparatus further comprising:
   a medical image display means that retrieves, from a medical image storage means that stores a multiplicity of medical images, a medical image related to the electronic medical record information displayed by the first or second electronic medical record information display means, and displays the retrieved medical image on the display device.

7. A medical information display apparatus, as defined in claim 5, the apparatus further comprising:
   a medical image display means that retrieves, from a medical image storage means that stores a multiplicity of medical images, a medical image related to the electronic medical record information displayed by the first or second electronic medical record information display means, and displays the retrieved medical image on the display device.

8. A medical information display apparatus, as defined in claim 4, the apparatus further comprising an examination information display means that retrieves, from an examination information storage means that stores a multiplicity of pieces of examination information, examination information related to the electronic medical record information displayed by the first or second electronic medical record information display means, and displays the retrieved examination information on the display device.

9. A medical information display apparatus, as defined in claim 5, the apparatus further comprising an examination information display means that retrieves, from an examination information storage means that stores a multiplicity of pieces of examination information, examination information related to the electronic medical record information displayed by the first or second electronic medical record information display means, and displays the retrieved examination information on the display device.

10. A medical information display apparatus, as defined in claim 1, wherein the timeline selection input receiving means receives an input by one of a mouse, a keyboard and a touch panel provided at the display device.

11. An operation method of a medical information display apparatus that includes: a timeline display means that displays a timeline on a display device; a timeline selection input receiving means that receives an input selecting a predetermined period on the timeline; an electronic medical record information retrieval means that retrieves electronic medical record information; an examination target region extraction means that extracts an examined region that is recorded in the electronic medical record information; and an examined-region position display means that displays an external view image on the display device in such a manner to superimpose a mark representing the examined region on the external view image, the method comprising:
   displaying, by the timeline display means, the timeline representing a time axis on the display device; receiving, by the timeline selection input receiving means, a selection input selecting a predetermined period on the timeline;
   obtaining, by the electronic medical record information retrieval means, a set of pieces of electronic medical record information by retrieving, from an electronic medical record storage means that stores a multiplicity of pieces of electronic medical record information, electronic medical record information about examination and treatment received by a predetermined person to be examined during the selected period;
   extracting, by the examination target region extraction means, all of at least one examined region that is recorded in the set of pieces of electronic medical record information;
   displaying, by the examined-region position display means, an external view image representing an external view of a human body on the display device, and superimposing one or more marks, each of which represents each of the extracted all of at least one examined region, at one or more positions corresponding to the examined region in the external view image; and receiving, via the timeline selection input receiving means, the selection of the predetermined period by setting a mark indicating a start time of the examination period and a mark indicating an end time of the examination period on the timeline.

12. A non-transitory computer-readable recording medium storing therein a medical information display program for causing a computer to function as:

a timeline display means that displays a timeline representing a time axis on a display device;

a timeline selection input receiving means that receives a selection input selecting a predetermined period on the timeline;

an electronic medical record information retrieval means that obtains a set of pieces of electronic medical record information by retrieving, from an electronic medical record storage means that stores a multiplicity of pieces of electronic medical record information, electronic medical record information about examination and treatment received by a predetermined person to be examined during the selected period;

an examination target region extraction means that extracts all of at least one examined region that is recorded in the set of pieces of electronic medical record information; and an examined-region position display means that displays an external view image representing an external view of a human body on the display device, and superimposing one or more marks, each of which represents each of the extracted all of at least one examined region, at one or more positions corresponding to the examined region in the external view image, wherein the timeline selection input receiving means receives the selection of the predetermined period by setting a mark indicating a start time of the examination period and a mark indicating an end time of the examination period on the timeline.

13. A medical information display apparatus, as defined in claim 1, wherein the external view image comprises a standard shape of a head, a chest, an abdomen, an arm, and a leg of the human body.

14. A medical information display apparatus, as defined in claim 1, wherein the examined-region position display means displays the mark representing each examined region based on a degree of importance of the mark.

15. A medical information display apparatus, as defined in claim 1, wherein the examined-region position display means displays the mark representing each examined region in different colors, the different colors being based on a degree of importance of the mark.

16. A medical information display apparatus, as defined in claim 8, wherein the examination information display means displays advice information related to health condition information and the electronic medical record information according to a user input.

17. A medical information display apparatus, as defined in claim 9, wherein the examination information display means displays advice information related to health condition information and the electronic medical record information according to a user input.

* * * * *